US00PP28793P2

(12) United States Plant Patent
Couturieux

(10) Patent No.: US PP28,793 P2
(45) Date of Patent: Dec. 26, 2017

(54) ***PHYSOCARPUS* PLANT NAMED 'COURIPHY01'**

(50) Latin Name: *Physocarpus opulifolius*
Varietal Denomination: Couriphy01

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 15/530,273

(22) Filed: Dec. 16, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — Audrey Charles

(57) ABSTRACT

A new and distinct cultivar of *Physocarpus* plant named 'Couriphy01', characterized by its whitish-pink colored flowers, dark green-colored mature foliage that turns dark burgundy in full sun, and moderately vigorous, upright-rounded growth habit, is disclosed.

1 Drawing Sheet

Latin name of genus and species of plant claimed: *Physocarpus opulifolius*.

Variety denomination: 'Couriphy01'.

BACKGROUND OF THE INVENTION

The present invention relates to a new and distinct cultivar of *Physocarpus* plant botanically known as *Physocarpus opulifolius* and hereinafter referred to by the cultivar name 'Couriphy01'.

The new cultivar originated in a controlled breeding program in Moyenmoutier, France during May 2005. The objective of the breeding program was the development of *Physocarpus* cultivars with a novel foliage color.

The new *Physocarpus* cultivar was the result of cross-pollination. The female (seed) parent of the new cultivar is DIABOLO 'Monlo', U.S. Plant Pat. No. 11,211, characterized by its creamy-white flowers, maroon-red colored foliage, and vigorous, upright slightly spreading growth habit. The male (pollen) parent of the new cultivar is 'Dart's Gold', not patented, characterized by its white-colored flowers, bright golden yellow foliage that ages with a bronze hue in fall, and moderately vigorous, compact-mounded habit. The new cultivar was discovered and selected as a single flowering plant within the progeny of the above stated cross-pollination during August 2006 in a controlled environment in Moyenmoutier, France.

Asexual reproduction of the new cultivar by softwood and hardwood cuttings since July 2010 in Moyenmoutier, France and Angers, France has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Couriphy01' as a new and distinct cultivar of *Physocarpus* plant:

1. Whitish-pink colored flowers;
2. Dark green-colored mature foliage that turns dark burgundy in full sun; and
3. Moderately vigorous, upright-rounded growth habit.

Plants of the new cultivar differ from plants of the female and male parents primarily in foliage color and growth vigor.

Of the many commercially available *Physocarpus* cultivars, the most similar in comparison to the new cultivar is Amber Jubilee 'Jefam', U.S. Plant Pat. No. 23,177. However, in side-by-side comparisons, plants of the new cultivar differ from plants of 'Jefam' in at least the following characteristics:

1. Plants of the new cultivar have an immature foliage color different from plants of 'Jefam';
2. Plants of the new cultivar have less growth vigor than plants of 'Jefam'; and
3. Plants of the new cultivar have a leaf shape different from plants of 'Jefam'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Couriphy01'. The plants were approximately 2-years old and grown in three-gallon containers for 1 year in an outdoor nursery in West Grove, Pa.

DETAILED BOTANICAL DESCRIPTION

Figure 1:
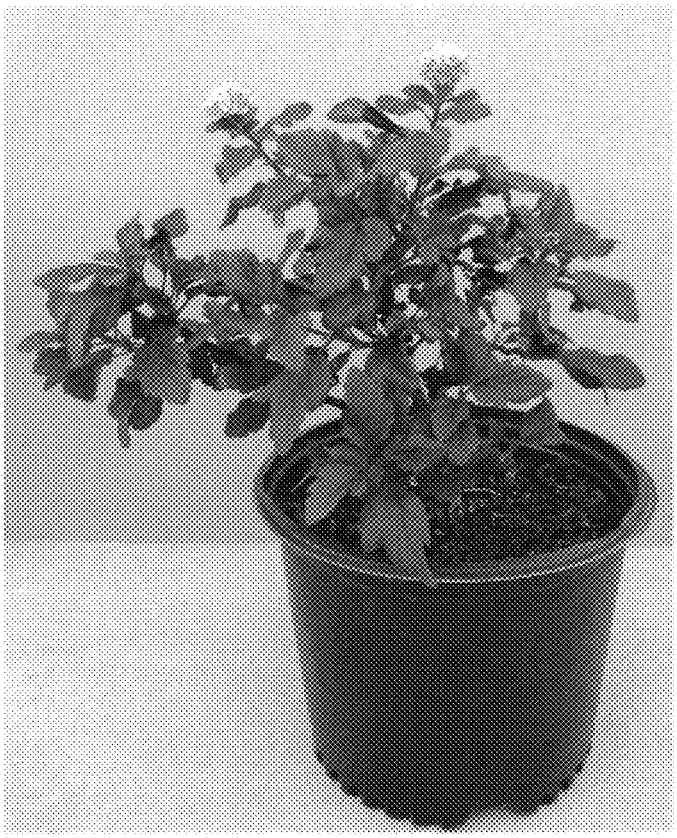
FIG. 1 illustrates a side view of the overall growth and flowering habit of 'Couriphy01'.
Figure 2:
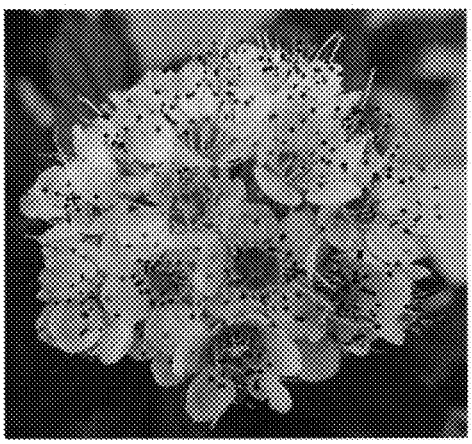
FIG. 2 illustrates a close-up view of a flower cluster of 'Couriphy01'
Figure 3:
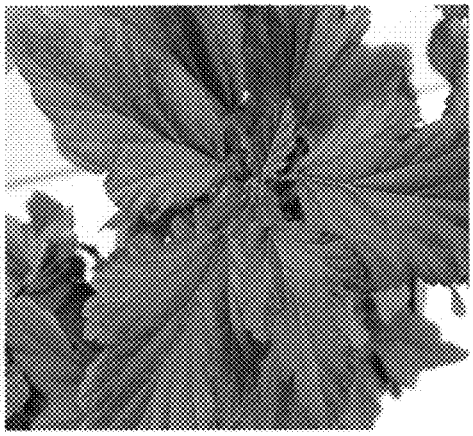
FIG. 3 illustrates a close-up view of the foliage of 'Couriphy01'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in October 2016 under natural light conditions in West Grove, Pa.

The following descriptions and measurements describe approximately 2-year old plants produced from cuttings from stock plants and grown in an outdoor nursery under conditions comparable to those used in commercial practice. The plants were grown in West Grove, Pa. for 1 year in three-gallon containers utilizing a soilless growth medium. Measurements and numerical values represent averages of typical plants.

Botanical classification: *Physocarpus opulifolius* cultivar Couriphy01.

Parentage:

*Female parent*.—DIABOLO 'Monlo', U.S. Plant Pat. No. 11,211.

*Male parent*.—'Dart's Gold', not patented.

Propagation:

*Type cutting*.—Softwood.

*Time to initiate roots*.—Approximately 15 days.

*Time to produce a rooted cutting*.—Approximately 65 days.

*Root description*.—Fibrous, white in color.

*Rooting habit*.—Freely branching.

Plant description:

*Growth habit and general appearance*.—Moderately vigorous, upright-rounded growth habit.

*Size*.—Height: Approximately 35.0 cm. Width: Approximately 35.0 cm.

*Branching habit*.—Freely branching, pinching enhances basal branching. Quantity of main lateral branches per plant: Approximately 7.

*Branch*.—Strength: Strong. Length: Approximately 15.0 cm to 20.0 cm. Diameter: Approximately 5.0 mm. Length of central internode: Approximately 2.0 cm. Texture: Rough and exfoliating. Color of young stems: 175A. Color of mature stems: 174B with exfoliating outer bark of 200A to 200C.

Foliage description:

*General description*.—Quantity of leaves per main branch: Approximately 37.0. Fragrance: Not detected. Form: Simple. Arrangement: Alternate.

*Leaves*.—Shape: Ovate with three lobes per leaf. Margin: Serrate. Apex of lobes: Acute. Base: Obtuse. Venation pattern: Pinnate. Length of mature leaf: Approximately 5.0 cm. Width of mature leaf: Approximately 3.0 cm. Texture of upper and lower surfaces: Glabrous. Color of upper surface of young foliage: 148A with an overlay of 200B giving a copper-like appearance with venation of NN137B. Color of lower surface of young foliage: 148A with venation of 148C. Color of upper surface of mature foliage: NN137A with venation of NN137A; in full sun foliage becomes dark burgundy 187B in color. Color of lower surface of mature foliage: 146B with venation of 146D.

*Petiole*.—Length: Approximately 1.5 cm. Diameter: Approximately 1.0 mm. Texture: Glabrous. Color: 174A on upper side and 199B on lower side.

Flowering description:

*Flowering habit*.—'Couriphy01' flowers freely in early to mid-summer.

*Lastingness of individual inflorescence on the plant*.—Approximately two to three weeks.

Inflorescence description:

*General description*.—Type: Corymb, not persistent. Shape: Hemispherical. Aspect: Facing upward and outward. Arrangement: Terminal and axillary. Fragrance: None detected. Quantity per plant: Approximately 4. Diameter: Approximately 3.5 cm. Depth: Approximately 2.0 cm.

*Peduncle*.—Strength: Strong. Aspect: Erect. Length: Approximately 1.0 cm. Diameter: Approximately 3.0 mm. Texture: Glabrous. Color: 175A.

Flower description:

*General description*.—Type: Single. Shape: Rotate. Quantity of fully-open flowers per inflorescence: Approximately 40. Appearance: Dull.

*Bud*.—Rate of opening: Generally takes 1 to 2 days for bud to progress from first color to fully-open flower.

*Bud just before opening*.—Shape: Elliptic. Length: Approximately 4.0 mm. Diameter: Approximately 4.0 mm. Texture: Glabrous. Color: 49D.

*Corolla*.—Diameter: Approximately 1.0 cm. Depth: Approximately 5.0 mm.

*Petals*.—Quantity: 5. Shape: Obovate. Margin: Entire. Apex: Obtuse. Base: Attenuate. Length: Approximately 4.0 mm. Width: Approximately 5.0 mm. Texture of upper and lower surfaces: Glabrous. Color of upper surface when first and fully open: 155B occasionally having a faint overlay of N74D most prominent at apex. Color of lower surface when first and fully open: 155B occasionally having a faint overlay of N74D most prominent at apex.

*Calyx*.—Diameter: Approximately 5.0 mm. Depth: Approximately 2.0 mm.

*Sepals*.—Quantity per flower: 5. Shape: Subulate. Apex: Sharply acute. Length: Approximately 4.0 mm. Width: Approximately 3.0 mm. Texture of upper (inner) surface: Glabrous. Texture of lower (outer) surface: Glabrous. Color of upper (inner) surface: 186C. Color of lower (outer) surface: 186C.

*Pedicel*.—Strength: Strong. Aspect: Erect. Length: Approximately 1.3 cm. Diameter: Less than 1.0 mm. Texture: Glabrous. Color: 153B.

*Reproductive organs*.—Androecium: Stamen quantity: Approximately 23 per flower. Stamen length: Approximately 3.0 mm. Filament length: Approximately 3.0 mm. Filament color: 69C. Anther shape: Oblong, dorsifixed. Anther length: Less than 1.0 mm. Anther color: 200A. Pollen amount: Sparse. Pollen color: 20A. Gynoecium: Pistil quantity: 4 per flower. Pistil length: Approximately 5.0 mm. Stigma shape: Capitate. Stigma length: Less than 1.0 mm. Stigma color: 163C. Style length: Approximately 5.0 mm. Style color: 157B. Ovary length: Less than 1.0 mm. Ovary color: 157C.

Seed and fruit production: Neither seed nor fruit production has been observed.

Disease and pest resistance: Resistance to pathogens and pests common to *Physocarpus* has not been observed.

What is claimed is:

1. A new and distinct cultivar of *Physocarpus* plant named 'Couriphy01', substantially as herein illustrated and described.

* * * * *